United States Patent [19]

Poncy et al.

[11] 4,155,494

[45] May 22, 1979

[54] SURGICAL GLOVE PACKAGE AND DONNING SYSTEM

[76] Inventors: Mark P. Poncy; George W. Poncy; Richard P. Poncy, all of 3670 E. Indus. Way, Riviera Beach, Fla. 33404

[21] Appl. No.: 819,842

[22] Filed: Jul. 28, 1977

[51] Int. Cl.² .............................................. A47J 51/06
[52] U.S. Cl. .................................... 223/111; 206/278; 206/438
[58] Field of Search ................ 223/111, 112; 206/278, 206/438 R, 439, 440; 2/16, 160, 161 R

[56] References Cited

U.S. PATENT DOCUMENTS

| | | | |
|---|---|---|---|
| 1,996,377 | 4/1935 | Hinchen | 223/111 |
| 4,002,276 | 1/1977 | Poncy et al. | 223/111 |
| 4,069,913 | 1/1978 | Harrigan | 206/438 |

*Primary Examiner*—Henry Jaudon
*Attorney, Agent, or Firm*—Lane, Aitken & Ziems

[57] ABSTRACT

In a surgical glove package, the cuff of the glove is stretched around a packaging ring so that the glove cuff extends radially back towards the center of the ring. Also extending around the ring is a flexible, transparent liner covering the outside surface of the glove and between the glove cuff and the ring so that the cuff holds the liner securely to the ring. The glove is donned and removed from the ring by using the liner to manipulate the glove package. The glove package can also be used in connection with an inflating apparatus which inflates the glove prior to inserting a hand into the inflated glove. The glove package components are assembled by means of a standpipe and blower combination, which inflates the liner and facilitates stretching the glove cuff around the ring.

14 Claims, 17 Drawing Figures

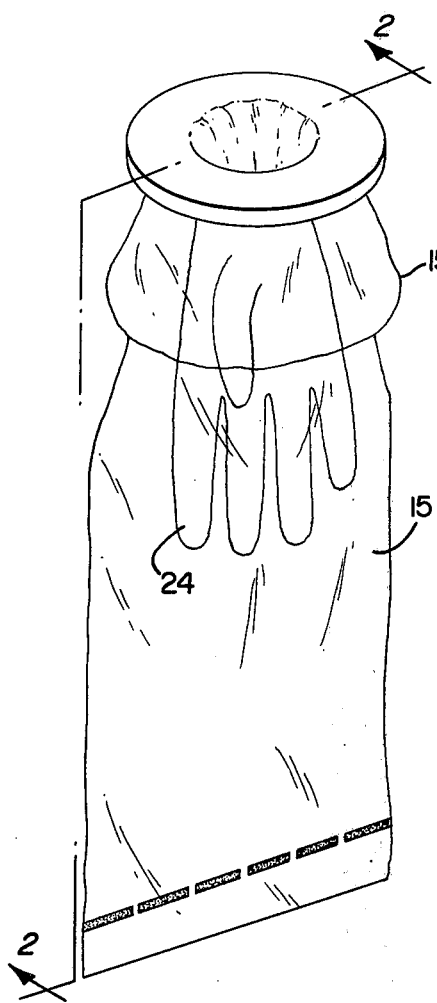
FIG. 1.
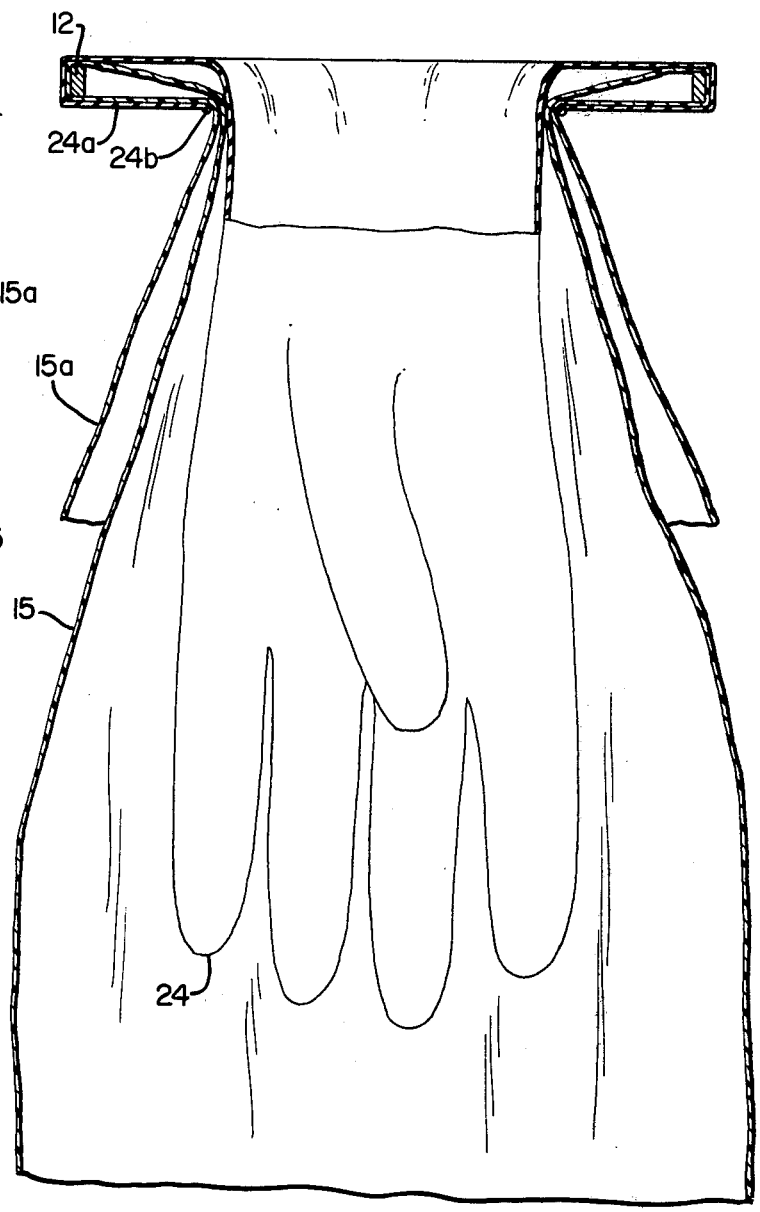
FIG. 2.
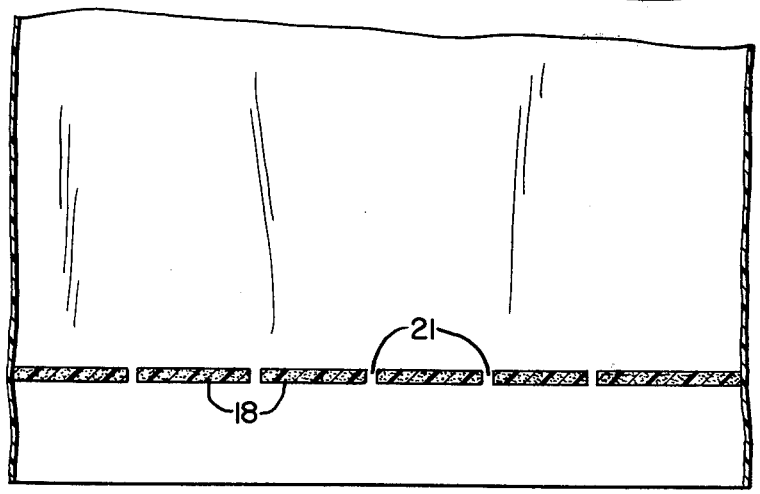

FIG. 8.
FIG. 7.
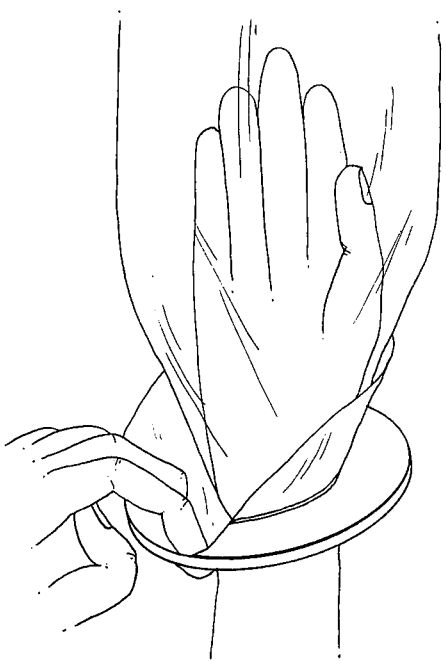
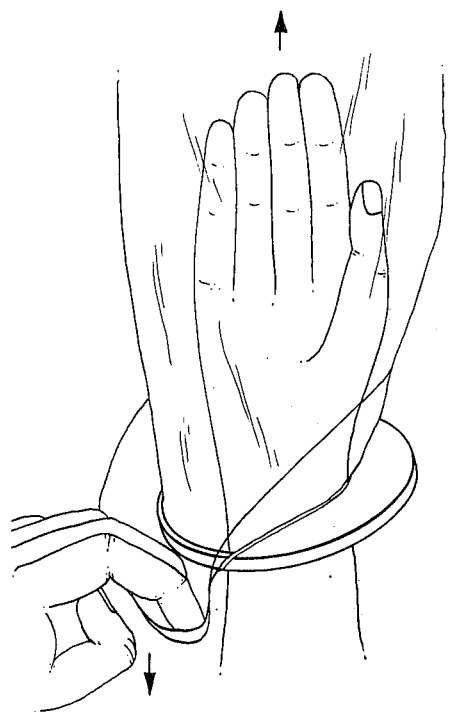
FIG. 9.
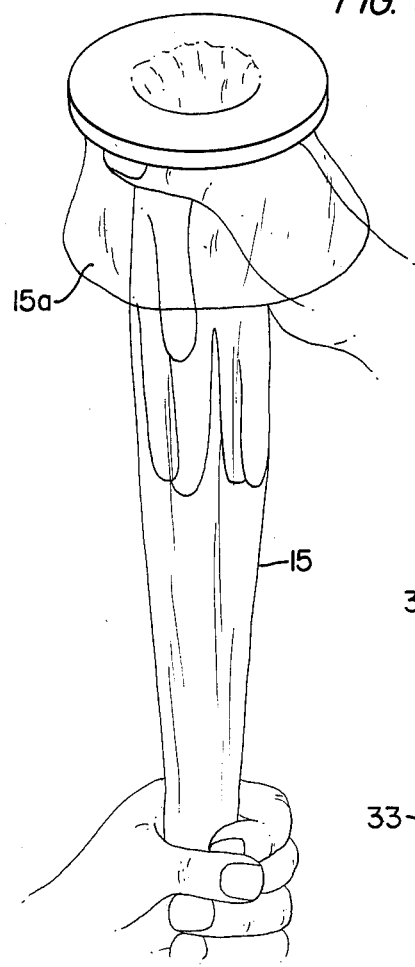
FIG. 10.
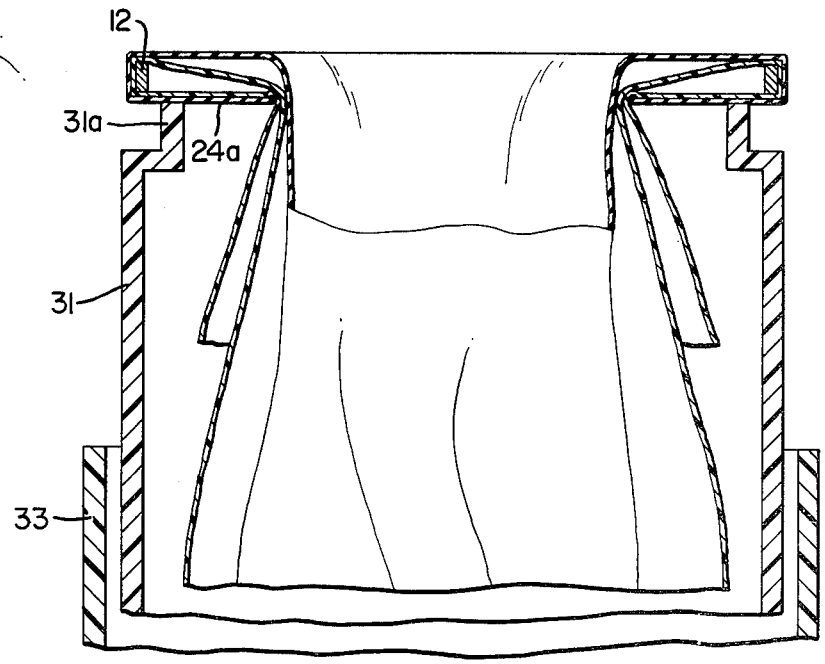

SURGICAL GLOVE PACKAGE AND DONNING SYSTEM

CROSS-REFERENCE TO RELATED APPLICATIONS

This application is related to application Ser. No. 797,384 entitled "Surgical Glove Package and Donning Method" filed May 16, 1977 by the inventors of this application. Application Ser. No. 797,384 is a continuation of application Ser. No. 618,336 filed October 1, 1975 which is now abandoned. Application Ser. No. 618,336 is related to U.S. Pat. No. 4,002,276 entitled "Surgical Glove Donning System" issued Jan. 11, 1977 to the inventors of this application on an application filed Aug. 1, 1975.

BACKGROUND OF THE INVENTION

A severe problem exists in the use of surgical sterile gloves, particularly in operating rooms where procedures for maintaining sterility have to be strictly followed. Specifically, the problem is that the surgeon and other operating room personnel must don the sterile gloves without letting the outside surfaces of the gloves or their sterile gowns come into contact with any non-sterile surface. This is a difficult procedure because, despite vigorous and prolonged scrubbing, the skin of the operating room personnel is not sterile and contact between the outer glove surfaces the bare hand, wrist and forearm must be avoided. In addition, while the inside surfaces of the glove may be touched, the contact between the skin and the inside surface of the glove should be confined to the portion of the glove as far inward and away from the edge of the cuff as possible. The cuff portion of the glove when the glove has been donned fits over the sleeve of the gown, and, during operation, the gown cuff will often pull out of the glove cuff to some extent, in which case the gown cuff formerly covered by the glove cuff will be exposed. As a result, any contamination that may have been present on the inside of the glove cuff will have been transferred to the gown cuff now exposed and the exposed, contaminated surface may come into contact with body tissue within the surgical wound.

In the present operating room procedure in which several persons must be gloved, a circulating nurse is employed who is not sterile and who will not take part in the sterile procedures. This circulating nurse is charged with responsibility of opening all the sealed packages containing sterile items but which are presumed to be contaminated on the outside. These items include sterile gowns which will be worn by all attending personnel and sterile gloves. All the sealed packages are designed in such a way that the outer envelope of each package may be peeled open and spread in a flat position on the table in such a way that the inner surfaces of the envelope constitute a sterile field which the circulating nurse does not touch. In a sterile glove package, the outer envelope contains inner folded paper wrap, which in turn contains a pair of sterile gloves.

After the circulating nurse has opened the packages, containing the sterile materials, a second nurse referred to as a scrub nurse, who will later assist in handling sterile objects, is gowned with the assistance of the circulating nurse in such a way that the circulating nurse does not touch the outside of the sterile gown. The gown has long sleeves which are tapered to fit snug around the wrists of the wearer. After being gowned, the scrub nurse proceeds with the self-donning of sterile gloves using either one of two alternative methods, one of which is referred to as the open method and the other is referred to as the closed method.

In the open method, the scrub nurse opens the inner folded wrapper containing the sterile gloves to expose the gloves lying side by side. The gloves have been packaged with a considerable portion of the cuff turned over on itself. The scrub nurse grasps the right glove with her left hand near the folded edge of the cuff portion while maintaining the area of contact between her left hand and the glove as far away as possible from the edge of the cuff. The nurse then inserts her right hand into the glove attempting full entry of the fingers into the tightly fitting glove by tugging with her left hand on the folded over cuff portion. Care must be taken at this point to avoid premature snapping back or unfolding of the cuff portion. To avoid this occurrence, the thumb of the hand being gloved may be hooked into the folded over cuff portion until full entry is made into the finger portion. The folded cuff portion is then unfolded and allowed to snap back along the wrist portion of the hand and over the cuff. In carrying out the unfolding of the cuff, care must be taken to avoid touching the outer glove surface and confining contact to the inner surface as far away as possible from the cuff edge. At the same time, care must also be exercised to make sure that the left hand of the scrub nurse does not touch the sterile gown cuff. This step of unfolding the cuff of the first glove is an extremely critical point in the open method and it is believed by operating room personnel that contamination occurs more than fifty percent of the time during this step of the procedure. Once the right hand is gloved, the left glove is picked up with the gloved right hand by inserting the gloved hand into the folded cuff portion of the glove. Because the outside surface of the glove on the gloved hand is sterile, contact between the gloves' outer surfaces is permitted. The left glove is pulled on by the gloved hand exerting pressure inside of the folded cuff portion and the cuff is unfolded and allowed to snap back along the wrist portion and over the left gown cuff. At this point, care must again be taken to avoid premature unrolling of the glove cuff to avoid contamination of the edge of the cuff that would result from contact with the skin at the wrist portion.

The high incidence of glove contamination which occurs in the open method has led to the adoption in some operating rooms of the closed method of donning the gloves. The closed method, while lessening the chance of contamination of the gloves, imposes a difficult and almost acrobatic technique upon the scrub nurse who must don the gloves without assistance. In the closed procedure, as in the open method, the scrub nurse is already gowned with the gown having full length tapered sleeves over which the cuff portions of the gloves will be snapped. In this method, instead of grasping the right glove with the bare fingers, the nurse grasps the glove through the gown sleeves. To carry out this technique, the nurse does not put her hands through the sleeve openings, but lets the gown sleeves cover her hands. The scrub nurse grasps the right glove in her left hand through the sleeve and positions the glove over her right wrist with the glove fingers pointing up the arm. Then, still working with her left hand through the left gown sleeve and with her right hand still inside the right sleeve, the nurse inserts the right sleeve cuff into the right glove cuff and snaps the right glove cuff over the right sleeve cuff. Then the nurse grasps the right sleeve cuff, now covered by the glove cuff, with the left hand still working through the left sleeve and pulls the right glove onto the right hand until as much entry into the fingers as can be achieved is effected. The process is then duplicated for the left hand except that the nurse does not work on the left glove through the right sleeve. The nurse, however, must maintain the ungloved left hand inside the sleeve until the left glove is snapped around the left sleeve cuff. The closed procedure is very difficult and requires a lot of practice to develop any proficiency in the procedure.

The above described procedures are concerned with the self-donning of the gloves by the scrub nurse and must be undertaken in order to provide a sterile nurse who can assist the others in the operating room in donning their gloves.

In assisting the donning of a second person, the scrub nurse, who is already gloved, picks up a sterile glove and places the fingers of both hands inside the folded over cuff portion exerting outward pressure in an attempt to stretch open the opening presented to the person to be donned. The donner, often the surgeon, then vigorously thrusts his hand up and into the glove. The nurse must maintain a steady force against this thrust by the surgeon who is attempting an initial thrust to gain access to the fingers of the glove. Almost in the same motion, the nurse thrusts forward and, by letting go of the glove cuff at the right moment, attempts to cause the cuff to snap over the surgeon's gown cuff without any rollover of the cuff edge.

Because of the difficulty in fully inserting hands into the gloves, the inner surface of the gloves must be heavily powdered to lubricate the glove surface relative to the hands. This powder in operation normally results in powder getting on the external surfaces of the glove. As a result, the surgeon must use sterile wipes to cleanse the glove surfaces of powder because the presence of powder particles in a surgical wound would aggravate the internal organs and tissue and would adversely affect the healing following surgery.

While sterile gloves are necessary with operating rooms, a greater number of sterile gloves are actually used in other procedures outside of operating rooms. Usually outside of the operating rooms, the person donning the glove must don the gloves without assistance. In many of these instances, a gown is not used, so the person donning the glove has no alternative but to use the open method of donning with its attendant greater risks of accidental contamination. In these instances, the contamination often occurs when attempts are made to prevent the cuff from rolling or in straightening out a cuff that has rolled over.

As indicated above, while procedures and requisites necessary to avoid contact with unsterile surfaces are strictly required, in actual practice, accidents of contamination are commonplace.

SUMMARY OF THE PRESENT INVENTION

The purpose of the present invention is to provide a sterile glove package which permits the sterile glove to be donned quickly, easily, and without assistance and without any powder appearing on the outside of the glove. In accordance with the present invention, the glove is packaged with a ring and a flexible liner covering the outside surface of the glove. The liner extends through the ring with the edge of the liner folded over the outside of the ring. The glove extends through the middle of the ring inside of the liner and the cuff of the glove is stretched around the outside of the ring with the edge of the cuff extending back in toward the middle of the ring so that the cuff defines a round opening through which the material of the liner and the hand and the finger portion of the glove extend. The ring of the package thus holds the cuff of the glove open for insertion of the hand into the glove.

With the above described package, the gloves can be donned very easily and with little danger of the outside glove surfaces coming into contact with the contaminated surface and also contact of the inside of the cuff of each glove and contaminated surfaces can be completely avoided except where the glove comes into contact with the wrist of the person wearing the glove beyond the end of the gown sleeve. The liner covering the outside surface of the glove provides a convenient microbial barrier through which the glove can be manipulated during the donning procedure to maintain the surface of the glove sterile. Moreover, because the liner covers the outside surface of the glove, the inside surface of the glove can be powdered with lubricating, moisture absorbing powder without any of the powder getting on the outside surface of the glove in contrast with present day packages in which powder is always all over the outside of the gloves as well as inside the gloves.

The glove package of the invention is also ideally suited for use with a glove inflating apparatus similar to that disclosed in U.S. Pat. No. 4,002,276, referred to above.

The glove inflating apparatus comprises a tube which has a mouth with an outside diameter a little smaller than the inside diameter of the packaging ring. The glove package is placed on the mouth of the tube with the radially inward extending cuff portion of the glove in contact with the mouth of the tube. This arrangement provides a good seal with the mouth of the tube when the pressure within the tube is reduced to inflate the glove.

BRIEF DESCRIPTION OF THE DRAWINGS

FIG. 1 is a perspective view of the glove package for the right hand;

FIG. 2 is a sectional view taken along the line 2—2 of FIG. 1;

FIGS. 6, 7 and 8 illustrates successive steps in donning the surgical glove on one hand;

FIG. 9 illustrates the initial step of preparing the glove package to be inflated by the glove inflating apparatus similar to that disclosed in U.S. Pat. No. 4,002,276;

FIG. 10 is a sectional view illustrating the glove package mounted on the inflating apparatus similar to that disclosed in U.S. Pat. No. 4,002,276;

DESCRIPTION OF THE PREFERRED EMBODIMENTS

Figure 3:
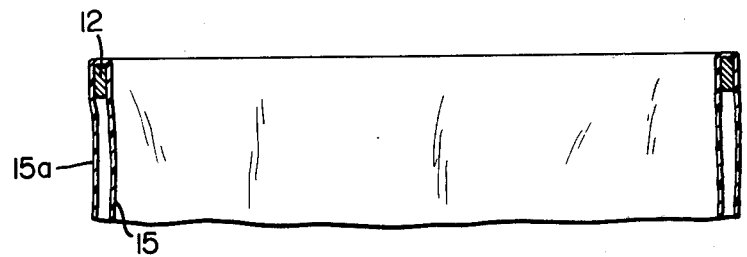
FIG. 3 illustrates how the liner is mounted on the ring of the package.

As shown in FIGS. 1 and 2, the glove package of the present invention comprises a packaging ring 12 which may be made of paperboard or may be molded from a rigid plastic such as styrene or high density polyethelene. A thin, transparent, flexible liner 15 in the form of a tube has one end extending up through the middle of the ring and turned down over the outside of the ring to provide a skirt 15a hanging down from the ring. The other end of the tube forming the liner 15 is closed by seal 18 extending across the other end of the tubular liner. The seal 18 is formed in a manner to leave small openings 21 so as to communicate the interior of the liner with the exterior. The seal 18 thus makes the liner 15 into a bag. A glove 24 made of thin, elastomeric material has its palm and finger portions extending down through the middle of the ring 12 into the interior of the liner 15. The cuff portion 24a of the glove is mounted on the ring by being stretched over the ring with enough overlap to go entirely around the ring so that the cuff 24a, which is under elastic tension, extends radially back toward the center of the ring. As shown in FIG. 2, the cuff edge 24b defines a circular hole through which the inner part of the liner 15 extending through the ring 12 as well as the skirt 15a is gathered. Because the elastomeric material of the glove cuff is stretched over the liner around the outside of the ring, it holds the liner securely mounted on the ring. Before the glove is mounted on the ring, the liner merely drapes vertically from the ring as shown in FIG. 3. As can be seen in FIG. 3, there is nothing to hold the liner on the ring except gravity until the glove cuff is lapped around the ring to hold the liner on the ring by the elastic tension under which the cuff is placed when it is stretched around the ring.

Figure 4:
FIG. 4 is a sectional view illustrating an alternative liner structure to more positively secure the liner to the ring.
Figure 5:
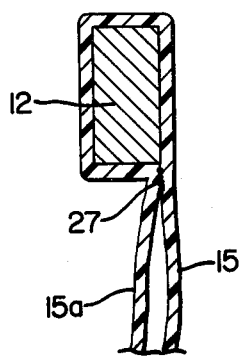
FIG. 5 is an enlarged view of the circled portion shown in FIG. 4.

Alternatively, the bag may be permanently secured to the ring as shown in FIGS. 4 and 5. As shown in these figures, the liner 15 is permanently secured to the ring by bonding the skirt portion 15a to the inner portion of the liner 15 hanging down through the ring. The bonding may be achieved by simple heat seal 27 just below the ring 12.

After the glove has been mounted on the ring and the lubricating powder is applied to the interior of the gloves, the powder will not get on the outside of the glove because of the liner 15. After the interior of the glove has been powdered, it is packaged with packaging material (not shown) and sterilized in a conventional manner as by ethelene oxide gas.

The gloves may be donned by an open method or a closed method which are analogous to the open and closed methods presently in practice described above. The closed method is preferably employed when the person donning the glove also wears a sterile gown with long sleeves as would normally be the case in operating rooms or wherever the sterility procedure is considered critical. In the closed method of donning the gloves in the glove package of the present invention, as in the closed method presently in practice, the person who intends to don the gloves in donning his gown does not thrust his hands fully through the cuffs of the gown sleeves, but maintains his hands within the gown cuffs so that the gown cuffs can act as a sterile interface when picking up the glove packages. A glove package is then simply grasped by the glove ring, through the gown sleeve of the opposing hand and the glove us pulled fully onto the hand simply as one would don an ordinary glove. Since a good grasp of the ring is readily obtained, the glove can be easily pulled on by pulling on the ring and no contamination can occur because of the protective liner on the glove and the interface action of the gown cuff. The second glove can then be donned like an ordinary glove with the first hand grasping the ring of the second glove package through the liner covering the first gloved hand.

Figure 6:
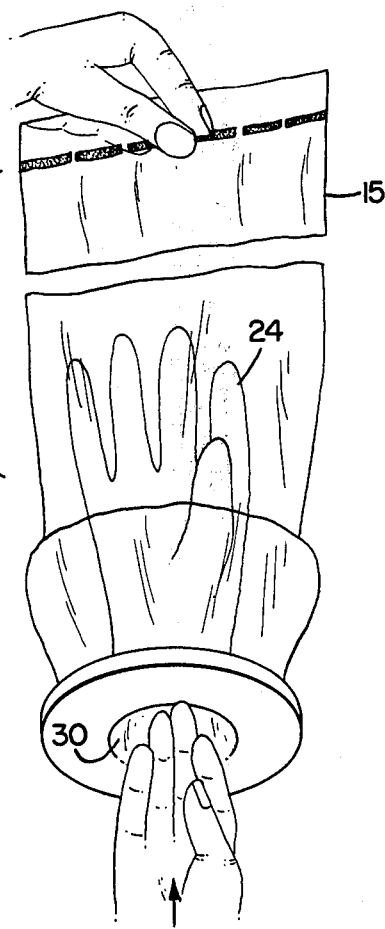

To don the glove in the glove package of the present invention by the open method, the sealed end of the liner 15 is grasped by the left hand allowing the ring to hang down vertically therefrom and the right hand is inserted partially into the opening 30 formed in the glove at the middle of the ring 12, as shown in FIG. 6. After the hand has been partially inserted into the opening 30, the fingers of the left hand are inserted inside the skirt 15a or, in other words, between the skirt 15a and the inner portion of the liner 15, as shown in FIG. 7. By pressure exerted on the liner at this point by the fingers, the glove is pulled fully onto the hand until the fingers and thumb are inserted fully into the glove. The procedure is then repeated with the left hand with the now gloved right hand performing the operations on the left hand through the liner which now covers the gloved right hand.

When both hands have been gloved by either method described above, each of the gloved hands will still be covered by the liner and, at this point, the person who has donned the glove, may touch and handle nonsterile surfaces through the liner as the sterility of the surfaces of the glove will be protected by the liner.

After both hands have been inserted fully into the gloves, as described above, the glove cuffs are released from the rings and liners and snapped over the wrists of the person donning the gloves as shown in FIG. 8. To release the cuff from the ring and liner, the skirt 15a, and, therefore, the cuff 24a, is pulled around the outside of the ring by the opposing hand allowing the cuff to snap over the wrist. When both of the gloves have been released from their respective rings and liners in this manner, the liner and ring may be removed from the right hand by grasping the liner and ring together with the left hand through the liner still covering the left hand. The ring and liner are then pulled partially off of the right hand turning the liner inside out as it is pulled off. To ensure that the liner turns inside out during this procedure, the right hand grasps the inside bottom portion of the liner as the ring and liner are being pulled over the right hand as described above. When the liner has been partially pulled off leaving the gloved right palm still covered by the partially inverted liner, the liner and ring on the left hand are removed completely from the left hand by grasping the ring and liner with the right hand through the partially inverted liner still covering the right hand and pulling the ring over the left hand. The left hand grasps the inside bottom portion of the liner covering the left hand so that the liner turns inside out as it is pulled off. The partially inverted liner on the right hand can then simply be dropped off the right hand by simply shaking the hand while it is positioned with the fingers pointing downwardly.

When the device is to be used in the inflating apparatus like that disclosed in U.S. Pat. No. 4,002,276, the glove package is held between the skirt 15a and the liner portion of the liner 15, as shown in FIG. 9, and the bottom or sealed end of the liner is pulled out to fully extend the liner. The package is then placed over the opening of the inflating apparatus, as shown in FIG. 10.

As shown in FIG. 10, the inflating apparatus, which has been modified slightly from the way it is disclosed in the patent, comprises an inner tube 31 and an outer tube 33 in which the inner tube telescopes. The inflating apparatus is arranged so that the axis of the telescoping tubes extends vertically. The inner tube 31 has a section 31a of reduced diameter at the mouth thereof. The inside diameter of the ring 12 of the glove package is of greater diameter than the outside diameter of the section 31a and the cuff portion 24a of the glove which laps over the ring and extends radially back toward the axis thereof rests upon the flat planar circular surface provided on the end of the tube 31 at the mouth thereof. The skirt 15a of the liner is arranged to be inside of the inner tube 31. After the glove package has been placed on the mouth of the inflating apparatus, as shown in FIG. 10, the glove is inflated in the same manner as described in the above mentioned patent.

As described in the patent, the glove is inflated by drawing the inner tube 31 out of the outer tube 33 creating a vacuum within the tubes which vacuum inflates the glove. As soon as the pressure is reduced within the tubes and the glove 24 begins to inflate, it draws the package down tightly against the mouth of the inner tube 31 and the elastic give of the material of the glove cuff 24a engaging the mouth of the inner tube 31 provides a good airtight seal. After the glove has been inflated, the inner tube 31 is latched in the extended position leaving the glove inflated as described in the above mentioned patent. The hand is then inserted in the inflated glove and the inner tube is unlatched and reinserted back into the outer tube sufficiently far so that a high pressure is produced within the inflating apparatus causing the glove cuff 24a to explode from the ring 12 and onto the wrist of the inserted hand. The gloved hand is then withdrawn from the telescoping tubes of the inflating apparatus and from the packaging ring.

Figure 11:
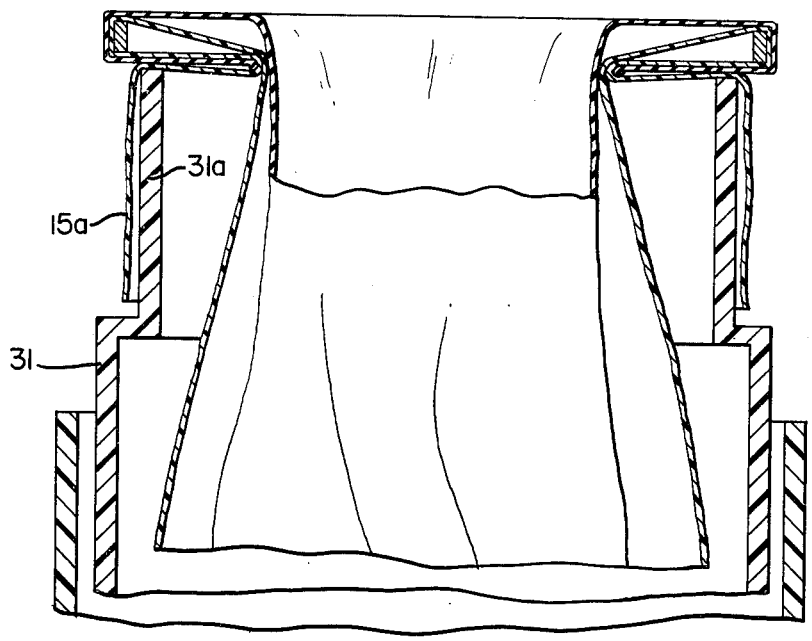
FIG. 11 is a sectional view illustrating an alternative glove inflating system with the glove package mounted on the inflating apparatus.

FIG. 11 shows an alternative system of employing the glove package with the inflating apparatus. In the system of FIG. 11, the length of the section 31a of the inner tube 31, which is of reduced diameter, has been increased and in this system, the skirt 15a of the liner is arranged to hang outside of this reduced diameter section instead of inside as in the system of FIG. 10. This arrangement permits the skirt of the liner to provide a protective barrier between the device and the glove donner's hands to reduce the possibility of accidental contact with the device during the donning procedure. In this instance, the liner, rather than the glove material, is in direct contact with the end of the inner tube 31. Nevertheless, the elasticity of the glove material, which is directly behind the liner material and which can flex in an axial direction, causes a good airtight seal to be produced between the mouth of the tube and the glove package when the pressure within the inflating apparatus is reduced causing the glove to inflate.

Figure 12:
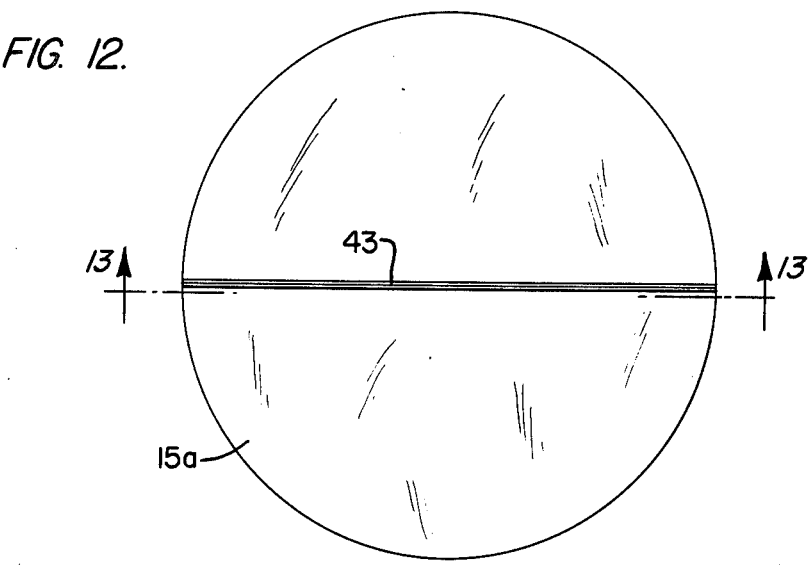
FIG. 12 illustrates a top plan view of an alternative glove package particularly adaptable for use with the inflating apparatus shown in FIG. 11.
Figure 13:
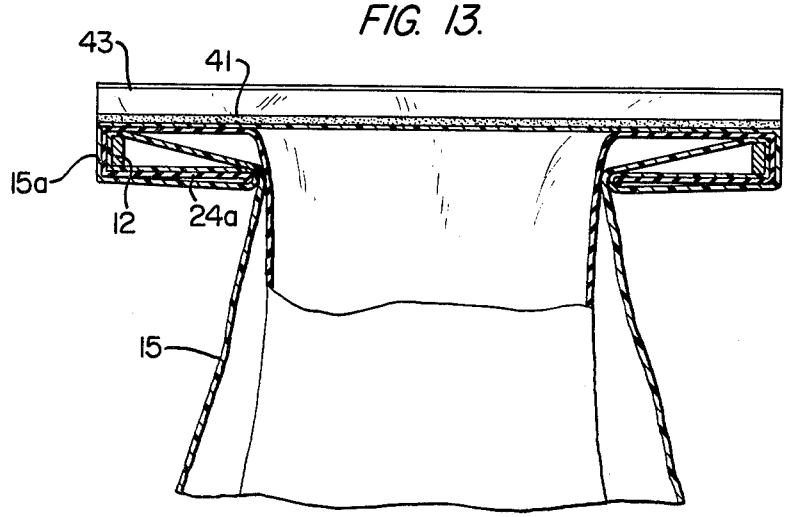
FIG. 13 is a sectional view taken along line 13—13 of FIG. 12.

FIGS. 12 and 13 illustrate a modified embodiment of the glove package, which embodiment is particularly suited for use with the system of FIG. 11. In the system shown in FIG. 12, the skirt 15a of the liner which extends beyond the cuff of the glove package is brought back up around the ring 12 and sealed together over the top of the ring along a seal 41 leaving flaps 43 extending beyond the seal. The seal 51 is formed so that it may be pulled apart by grasping the flaps 43. In this arrangement, the liner 15 completely encloses both the inside and outside surfaces of the glove in the glove package.

When the embodiment of FIGS. 12 and 13 is employed with the system of FIG. 11, the package is placed over the mouth of the inner tube 31 and then the flaps 43 are pealed apart. The skirt 15a of the liner is then draped about the extended reduced diameter section 31a, as shown in FIG. 11.

Figure 14:
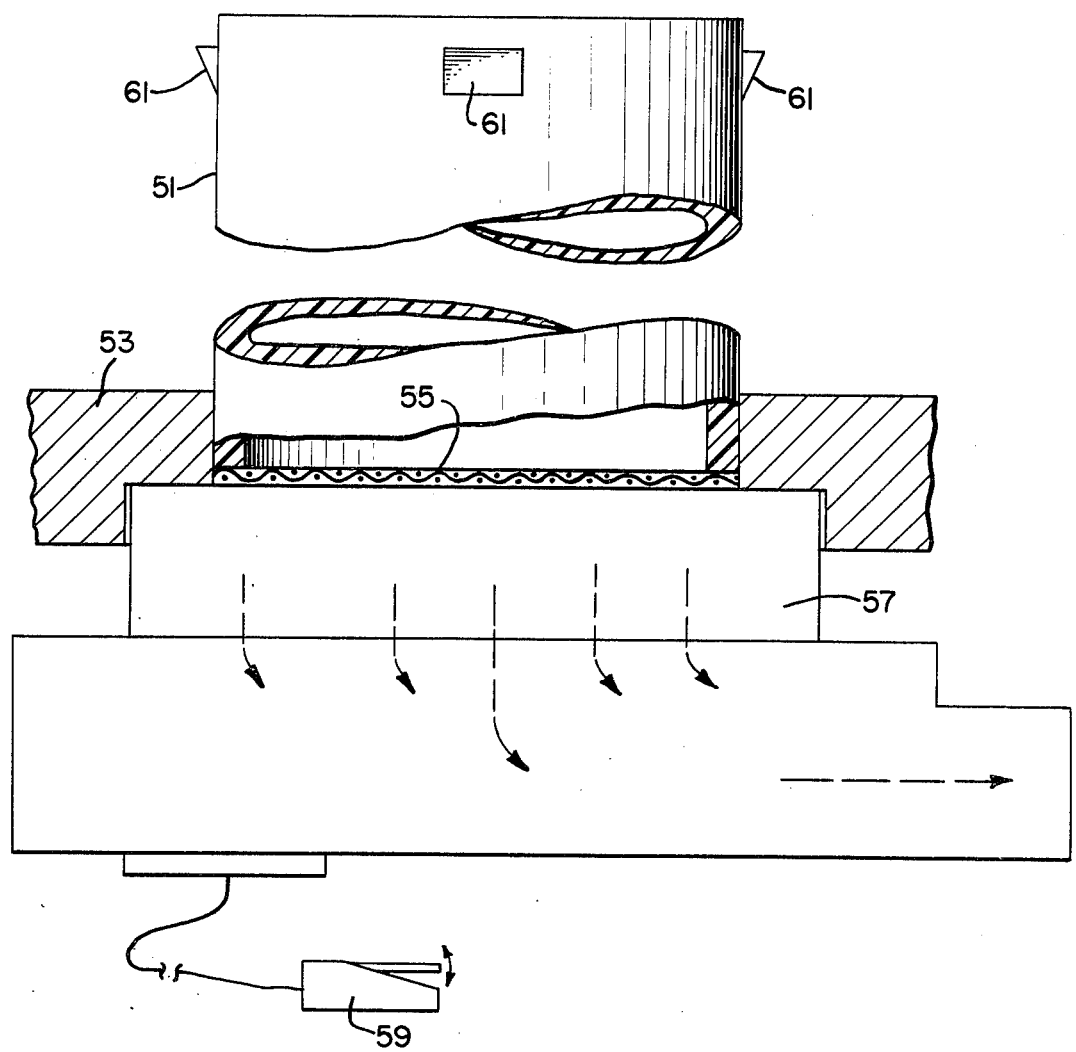
FIG. 14 is a partial sectional view illustrating the apparatus used for mounting the elastomeric glove with its liner on the packaging ring.

As shown in FIG. 14, which illustrates the apparatus for mounting the elastomeric glove 24 on the packaging ring 12, a standpipe 51 is mounted in a table top 53. The lower end of the standpipe 51 is closed by a mesh screen 55. A blower 57, operated by a foot treadle 59 is provided to draw air down through the standpipe 51. Four wedgeshaped lugs 61 are distributed around the outside surface of the standpipe 51 near the top thereof. The standpipe 51 has a diameter slightly less than the diameter of the packaging ring 12 so that the packaging ring can be rested on the lugs 61 as shown in FIG. 15.

Figure 15:
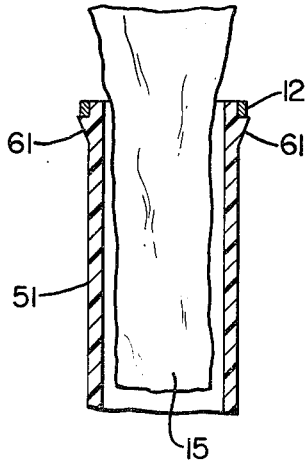
FIGS 15-17 are partial sectional views of the mounting apparatus shown in FIG. 13 illustrating the steps of mounting the glove and liner on the packaging ring.
Figure 16:
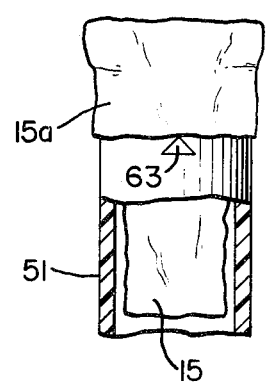
Figure 17:
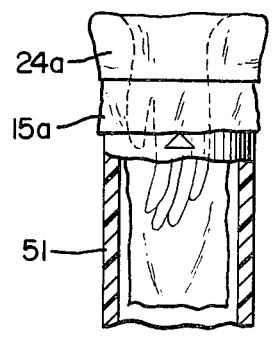

FIGS. 15-17 illustrate how the liner and glove are mounted on the packaging ring. In FIG. 15, the packaging ring 12 is resting on the lugs 61 without the liner and the glove mounted on the ring. As shown in FIG. 15, the liner 15 is first dropped into the standpipe and the blower is turned on to suck the liner down and keep it open against the standpipe wall. The skirt 15a of the liner 15 is then folded over the ring 12 down around the outside of the standpipe wall and is pulled down to an index mark 63 on the standpipe wall against the suction created by the blower on the liner, as shown in FIG. 16. The finger and hand portion of the glove 24 is then dropped into the open liner within the standpipe and the cuff portion 24a is stretched around the ring down around the outside of the standpipe encapsulating the ring and the liner as shown in FIG. 17. The cuff of the glove is brought down to about 1½ inches below the top of the standpipe. The ring is then grasped through the glove and liner and sharply pulled upward and off of the pipe. The cuff portion 24a of the glove extending down around the outside of the standpipe will immediately recover from its stretched state and fold to extend radially in toward the axis of the ring leaving an open circle through which the liner and palm and finger portion of the glove extend. The amount of the glove cuff portion radiating inwardly towards the center of the ring 12 will correspond to the amount of cuff portion which has been brought down along the outside wall of the standpipe below the bottom edge of the ring 12.

If the liner is to be sealed to the ring 12 as shown in FIGS. 4 and 5, then the liner must be heat sealed around the ring before the ring is placed on the standpipe. The glove is then mounted on the ring in the same manner as described above.

The above described glove package and donning system makes it possible for other persons desiring to put on the sterile gloves to very quickly and easily don the gloves without danger of contamination and without the need for the assistance of a second person. Moreover, the donning of the sterile glove is achieved by means of a very convenient glove package.

The above description is of preferred embodiments of the invention and many modifications may be made thereto without departing from the spirit and scope of the invention which is defined in the appended claims.

We claim:

1. A surgical glove package comprising a packaging ring, an elastomeric glove having its cuff stretched around the outside of said ring to extend over both axial ends of said ring with the edge of said cuff extending under elastic tension radially back toward the center of said ring past the inner radial edge of said ring to define an opening, the palm and finger portion of said glove passing through said opening.

2. A surgical glove package is recited in claim 1, further comprising a tubular flexible liner covering the outside surface of said glove and secured to said ring between the cuff portion of said ring.

3. A surgical glove package as recited in claim 2, wherein said liner is held on said ring solely by the cuff of said glove being stretched around said ring and holding said liner against said ring by the elasticity of the said cuff portion.

4. A surgical glove package as recited in claim 2, wherein said liner is folded over said ring and is sealed to itself to secure said liner to said ring.

5. A surgical glove package as recited in claim 2, wherein said liner passes through said ring and is folded over said ring to define a skirt portion which is sufficient length to pass through said opening defined by the edge of said cuff.

6. A surgical glove package as recited in claim 5, wherein said skirt portion extending through said opening is folded back over said ring and is sealed together to enclose the inside surface of said glove.

7. A surgical glove package as recited in claim 2, wherein the opposite end of said liner from that secured to said ring is closed to define a bag enclosing the outside surface of said glove.

8. A surgical glove package as recited in claim 7, wherein the end of said liner is closed by a seal joining the two sides of said liner together near the end thereof with gaps being provided in said seal to permit communication between the interior of said liner and the exterior of said liner.

9. A surgical glove package as recited in claim 2, wherein said liner is transparent.

10. A surgical glove donning system comprising a glove package having a packaging ring and an elastomeric glove with the cuff portion of said glove stretched around the outside of the ring over both axial ends of said ring with the edge of said cuff portion extending under elastic tension radially back toward the middle of said ring past the inner radial edge of said ring to define an opening and with the palm and finger portion of said glove passing through said opening; and an inflating apparatus having a tube with an open end designed to receive said glove package, said tube having a planar circular surface, the outside diameter of said tube at said open end being less than the inside diameter of said packaging ring, said cuff portion of said glove extending sufficiently far back toward the center of said ring so that said cuff portion can rest upon said planar circular surface, said inflating apparatus including means to reduce the pressure within said tube; whereby when said glove package is placed upon the open end of said tube with the cuff portion of said glove resting upon said planar circular surface and the pressure within said tube is reduced, the palm and finger portion of said glove will inflate to facilitate entry of a hand into said glove.

11. A glove donning system as recited in claim 10, wherein said glove package includes a liner covering the outside surface of said glove and secured to said packaging ring.

12. A glove donning system as recited in claim 11, wherein said liner passes through said ring and is folded over the outside thereof to define a skirt portion, said skirt portion being sufficiently long to pass through said opening defined by the edge of said cuff portion and to be brought back out over the outside of said tube.

13. A method of donning an elastomeric sterile glove comprising packaging said glove with the cuff portion of said glove stretched around the outside of a packaging ring over both axial ends of said ring with the edge of said cuff portion extending under elastic tension radially back toward the center of the ring past the inner radial edge of said ring with the palm and finger portion of the glove passing through the opening defined by the edge of said cuff portion, and with a flexible liner covering the outside surface of said glove and folded over said ring between said cuff portion and said ring to provide a skirt which extends through said opening defined by the edge of said cuff portion; inserting the hand to be donned through said ring into the palm and finger portion of said glove; and then releasing said cuff portion of said glove from said ring by manipulating the part of said cuff portion that extends past the inner radial edge of said ring, said manipulating being carried out by fingers acting through the thickness of the material of said skirt to pull said cuff portion off of said ring and onto the wrist of said hand.

14. A method of assembling an elastomeric glove, a packing ring and a tubular liner comprising placing said ring at the top of a pipe around the outside thereof and positioning said tubular liner within said pipe with a skirt of said liner positioned to hang down around the outside of said pipe covering said ring, positioning the palm and finger portion of said glove within said pipe and stretching the cuff portion of said glove over the end of said pipe down around the outside thereof to cover said ring and to partially cover said skirt, then removing said ring from said pipe so that when the stretched cuff portion of said glove recovers, it remains stretched around said ring and extends radially back toward the center of said ring drawing the skirt portion of said liner back toward the center of said ring and with the palm and finger portion of said glove extending through the opening defined by the cuff of said glove.

* * * * *